(12) United States Patent
Adams

(10) Patent No.: US 6,979,332 B2
(45) Date of Patent: Dec. 27, 2005

(54) SURGICAL MICRO-RESECTING INSTRUMENT WITH ELECTROCAUTERY AND CONTINUOUS ASPIRATION FEATURES

(75) Inventor: Kenneth M. Adams, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 233 days.

(21) Appl. No.: 10/700,856

(22) Filed: Nov. 4, 2003

(65) Prior Publication Data

US 2005/0096649 A1 May 5, 2005

(51) Int. Cl.[7] ............................................. A61B 18/18
(52) U.S. Cl. ................. 606/45; 47/170; 47/49
(58) Field of Search ................. 606/1, 41, 45, 606/46, 48–50, 167, 170, 171, 180; 604/21, 604/22; 48/49, 170

(56) References Cited

U.S. PATENT DOCUMENTS

| | | |
|---|---|---|
| 3,844,272 A | 10/1974 | Banko |
| 4,760,317 A | 7/1988 | Hetzel et al. |
| 5,195,959 A | 3/1993 | Smith |
| 5,217,457 A | 6/1993 | Delahuerga et al. |
| 5,364,395 A | 11/1994 | West, Jr. |
| 5,707,402 A | 1/1998 | Heim |
| 5,730,752 A | 3/1998 | Alden et al. |
| 5,782,795 A | 7/1998 | Bays |
| 5,797,907 A | 8/1998 | Clement |
| 5,810,809 A | 9/1998 | Rydell |
| 5,904,681 A | 5/1999 | West, Jr. |
| 5,904,698 A | 5/1999 | Thomas et al. |
| 5,908,419 A | 6/1999 | Hahnen et al. |
| 5,913,857 A | 6/1999 | Ritchart et al. |
| 5,922,003 A | 7/1999 | Anctil et al. |
| 5,925,040 A | 7/1999 | Nardella et al. |
| 5,941,876 A | 8/1999 | Nardella et al. |
| 5,951,548 A | 9/1999 | DeSisto et al. |
| 5,951,551 A | 9/1999 | Erlich |
| 5,957,881 A | 9/1999 | Peters et al. |
| 6,007,533 A | 12/1999 | Casscells et al. |
| 6,022,362 A | 2/2000 | Lee et al. |
| 6,032,673 A | 3/2000 | Savage et al. |
| 6,346,107 B1 | 2/2002 | Cucin |

(Continued)

FOREIGN PATENT DOCUMENTS

DE       196 41 563 A1       10/1996

(Continued)

OTHER PUBLICATIONS

XoMed Product Release, "RAD 55® & RAD 60 X-TREME®"; Sep. 1998.

(Continued)

*Primary Examiner*—Roy D. Gibson
(74) *Attorney, Agent, or Firm*—Timothy A. Czaja; Trevor D. Arnold

(57) ABSTRACT

A surgical micro-resecting instrument including an outer tubular member, an inner tubular member, a hub assembly, and an electrical insulator. The outer tubular member is formed of an electrically conductive material and defines a proximal section, a distal section, and a lumen. The distal section forms an axial passage distal a cutting window, both of which are fluidly connected to the lumen. The inner tubular member is disposed within the lumen and defines a distal portion that forms a cutting tip. The hub assembly maintains the inner and outer tubular members. The electrical insulator covers a region of the outer tubular member distal the hub assembly. In this regard, at least the cutting window is not covered by the electrical insulator for cauterizing contacted tissue via the energy. The axial passage facilitates continuous aspiration.

37 Claims, 9 Drawing Sheets

U.S. PATENT DOCUMENTS 6,663,628 B2    12/2003   Peters
2002/0038122 A1 *  3/2002  Peters .................... 606/45

FOREIGN PATENT DOCUMENTS

DE   196 41 564 A1   10/1996
DE   299 14 180 U1    8/1999
GB       2205045     11/1998

OTHER PUBLICATIONS

Charles M. Myer, III, M.D., et al., "Use of a Laryngeal Micro Resector System", pp. 1165-1166; Jul. 1999.

XoMed Advertisement, "Sinus Surgery Products", 5 pgs.

Michael Friedman, M.D., et al., "A Safe, Alternative Technique for Inferior Turbinate Reduction", pp. 1834-1837; Nov. 1999.

XoMed Surgical Technique Brochure, "Powered Laryngeal Surgery Using the Angle-Tip RAD Airway™ Blades", pp. 1-8.

XoMed Product Release, "SKIMMER™ Angle-Tip Laryngeal Blades", 1 pg; ©1998.

XoMed Advertisement, "Lose the Laser", 2 pgs; Aug. 1998.

Daniel G. Becker, M.D., "Technical Considerations in Powered Instrumentation", Otolaryngologic Clinics of North America, vol. 30, No. 3, pp. 421-433; Jun. 1997.

* cited by examiner

SURGICAL MICRO-RESECTING INSTRUMENT WITH ELECTROCAUTERY AND CONTINUOUS ASPIRATION FEATURES

BACKGROUND

The present invention relates generally to surgical micro-cutting instruments. More particularly, it relates to a surgical micro-resecting instrument integrating both mechanical and electrical current cutting as well as facilitating continuous aspiration.

Surgical cutting instruments in which an elongated inner member is rotated within an elongated outer tubular member have become well accepted in surgical procedures where access to the surgical site is gained via a narrow portal or passage. Typically, the outer tubular member includes a distal section terminating at a closed distal end and defining a cutting port or window proximal the distal end, and the inner member includes a distal portion forming a cutting tip for cutting bodily tissue at the cutting window. Proximal ends of the inner and outer members are commonly secured to hubs that, in turn, are attached to a power handpiece for rotating and/or oscillating the inner member relative to the outer tubular member. The cutting tip of the inner member can have various configurations specific to the surgical procedure in question (e.g., cutting, resecting, abrading, shaving, etc.), with the cutting window being suitably configured to cooperate with the particular configuration of the cutting tip. Often, the inner member is tubular so that the loose tissue resulting from a cutting, resecting, or abrading procedure can be aspirated through the hollow lumen of the inner tubular member via the cutting window. With specific reference to ENT applications, such as ethmoidectomy, sinus surgery, adenoidectomy, laryngeal surgery, etc., extremely sharp, micro-resecting blades or cutting tips are typically employed to effectuate the procedure.

The above-described surgical instruments rely upon a mechanical cutting action to resect, cut, shave, abrade, etc., the tissue in question. With respect to ENT procedures, mechanical-type, micro-resecting instruments are highly viable and present distinct advantages over other available devices. For example, $CO_2$ lasers are available. However, laser-based systems are expensive and present the distinct risk of thermal trauma or burns.

Efforts have been made to improve upon the design of surgical-resecting instruments. For example, the blade or cutting tip configuration can be optimized for certain applications. Further, so as to facilitate access to certain bodily areas, the surgical cutting instrument has been modified from a generally straight form to one having a fixed- or variable-angle design.

Often times, during an ENT micro-resecting procedure, it is necessary to coagulate or otherwise stem bleeding at the target site to provide hemostasis. The accepted technique for effectuating hemostasis is to remove the micro-resecting instrument and deploy a separate coagulation device. While necessary, this technique is highly time consuming. To overcome this problem, efforts have been made to develop a surgical micro-resecting instrument providing an integrated electrocautery feature, such as that described in U.S. patent application Ser. No. 09/961,543, filed Sep. 24, 2001, the teachings of which are incorporated herein by reference. While adequately eliminating the need for a separate coagulation device, these and other techniques may give rise to other concerns. For example, the exposed, energized surface area of the instrument is often times relatively large, potentially leading to less than optimal energy distribution at the target site. Additionally, and similar to other micro-resecting instruments, it is difficult, if not impossible, to adequately aspirate blood and other bodily tissue into and through the instrument, especially when the cutting window is "closed" by the cutting tip.

Surgical micro-resecting blade instruments continue to be extremely useful. Recent improvements to incorporate an electrocautery feature into the instrument appear promising. However, a need exists for a surgical micro-resecting instrument incorporating an optimized electrocautery feature that facilitates continuous aspiration where desired.

SUMMARY

One aspect of the present invention provides a surgical micro-resecting instrument including an outer tubular member, an inner tubular member, a hub assembly, and an electrical insulator. The outer tubular member is formed of an electrically conductive material and defines a proximal section, a distal section, and a lumen. Further, the distal section forms a cutting window and an axial passage, both of which are fluidly connected to the lumen. In this regard, the axial passage is formed distal the cutting window. The inner tubular member is disposed within the lumen of the outer tubular member and defines a proximal portion and a distal portion. The distal portion forms a cutting tip. The hub assembly maintains the proximal section of the outer tubular member and the proximal portion of the inner tubular member. Finally, the electrical insulator covers a region of the outer tubular member distal the hub assembly. To this end, at least the cutting window is not covered by the electrical insulator. With this configuration, the cutting tip is available for resecting tissue. When necessary, an electrical current can be applied to the outer tubular member, with the exposed portion of the distal section cauterizing contacted tissue via the energy. In one embodiment, the insulator is a dielectric material coated onto the outer tubular member.

Yet another aspect of the present invention relates to a surgical micro-resecting system for use in ENT procedures. The system includes a micro-resecting instrument, a powered surgical handpiece, an energy source, and wiring. The micro-resecting instrument includes an outer tubular member, an inner tubular member, a hub assembly, and an electrical insulator. The outer tubular member is formed of an electrically conductive material and defines a distal section and a lumen, with the distal section forming a cutting window and an axial passage distal the cutting window, both of which are open to the lumen. The inner tubular member is disposed within the lumen of the outer tubular member and defines a distal portion forming a cutting tip. The hub assembly is connected to, and maintains, the outer tubular member and the inner tubular member. Finally, the electrical insulator covers a region of the outer tubular member distal the hub assembly, with at least the cutting window being free of the insulator. The powered surgical handpiece is coupled to a proximal end of the inner tubular member, and is configured to drive the inner tubular member relative to the outer tubular member as part of a micro-resecting procedure. Finally, the energy source is electrically connected to the outer tubular member via the wiring. With this configuration, activation of the powered surgical handpiece initiates resecting of tissue. Additionally, activation of the energy source effectuates tissue cauterization via delivery of energy to the region of the outer tubular member not otherwise covered by the insulator. In one embodiment, the inner tubular member forms an axial opening distal the cutting tip, with the axial passage and the axial opening being fluidly connected to an internal lumen of the inner tubular member. The internal lumen, in turn, is connected to a vacuum source that facilitates aspiration through the inner tubular member via the axial opening and axial passage.

Yet another aspect of the present invention relates to a method for performing a micro-resecting operation at a target site of a patient as part of an ENT surgical procedure. The method includes providing a micro-resecting instrument including an outer tubular member, an inner tubular member, a hub assembly, and an electrical insulator. The outer tubular member has a lumen and a distal section forming a cutting window and an axial passage distal a cutting window, with the axial passage being fluidly connected to the lumen. The inner tubular member is disposed within the lumen and has a distal portion forming a cutting tip. The hub assembly is connected to, and maintains, the inner and outer tubular members. The electrical insulator covers a region of the outer tubular member distal the hub assembly, such that at least the cutting window remains exposed relative to the insulator. The distal section of the outer tubular member is delivered to the target site such that the cutting window is located at the target site and the cutting tip is located within the cutting window. The inner tubular member is driven relative to the outer tubular member such that the cutting tip resects tissue at the target site to effectuate a portion of an ENT procedure. Energy is supplied to an exposed region of the distal section of the outer tubular member. Finally, tissue at the target site is cauterized via the energized, exposed region of the outer tubular member. In one preferred embodiment, the method further includes continuously aspirating the target site while the inner tubular member is positioned such that the cutting tip closes the cutting window.

DETAILED DESCRIPTION

Figure 1:
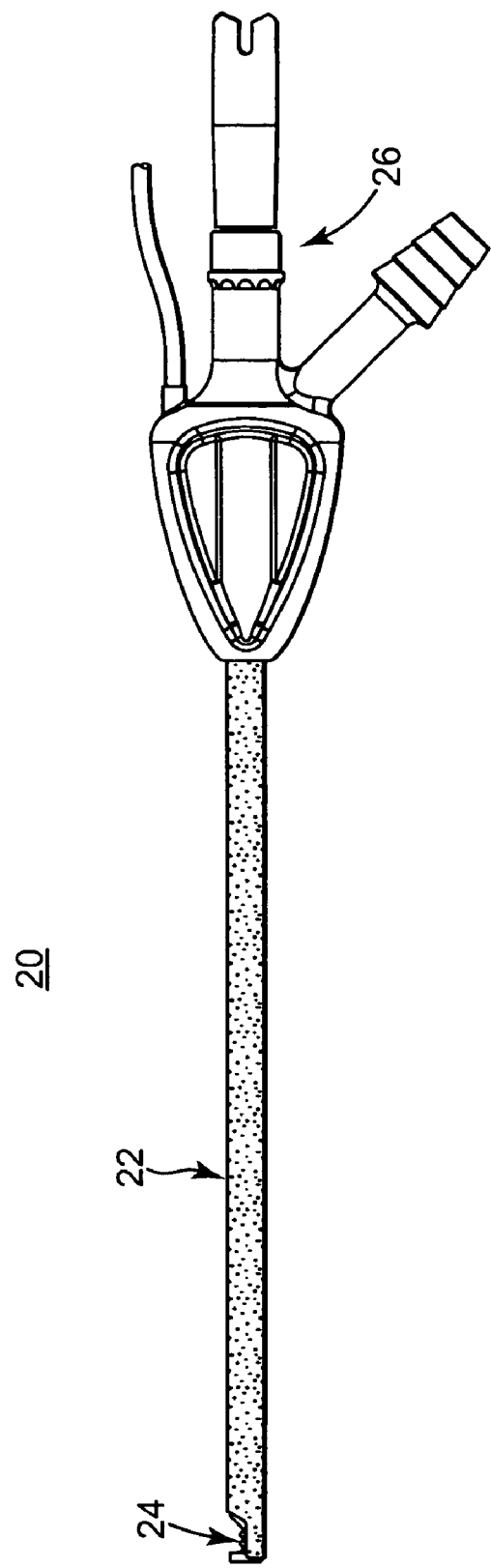
FIG. 1 is a side view of a surgical micro-resecting instrument in accordance with the present invention.

One embodiment of a surgical micro-resecting instrument or blade 20 in accordance with the present invention is illustrated in FIG. 1. The surgical instrument 20 includes an outer tubular member 22, an inner tubular member 24 (a majority of which is hidden in the view of FIG. 1), and a hub assembly 26. The components 22–26 are described in greater detail below. In general terms, however, the inner tubular member 24 is coaxially disposed within the outer tubular member 22. The hub assembly 26 maintains the inner tubular member 24 relative to the outer tubular member 22 in a manner that allows the inner tubular member to oscillate and rotate.

Figure 2:
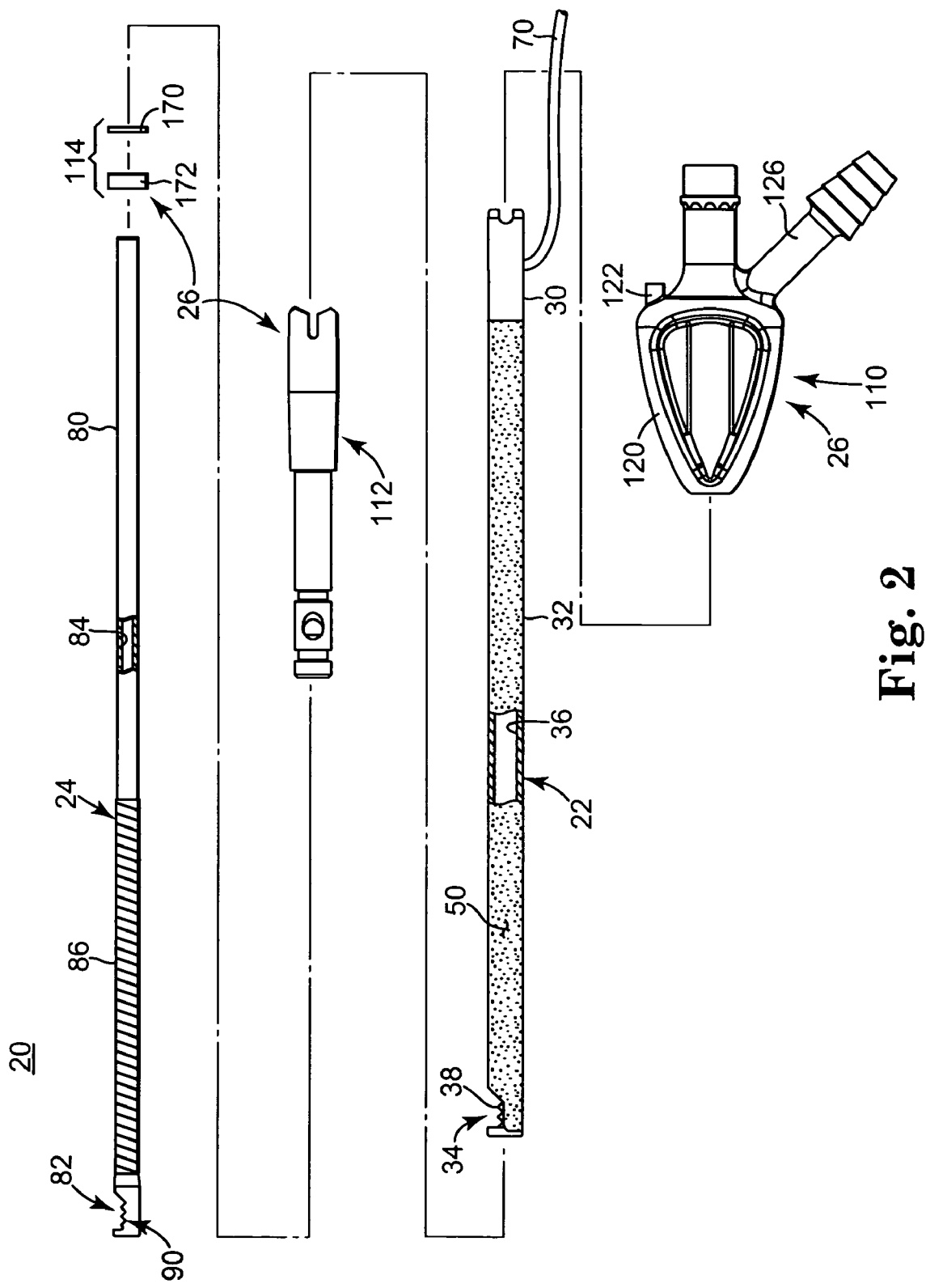
FIG. 2 is an exploded side view of the micro-resecting instrument of FIG. 1.

With additional reference to the exploded view of FIG. 2, the outer tubular member 22 is formed as an elongated tube, defining a proximal section 30, an intermediate section 32, and a distal section 34. A lumen 36 extends from the proximal section 30 to the distal section 34. Finally, the distal section 34 forms a cutting window 38 and an axial passage 40 (referenced generally in FIG. 2), both of which are fluidly connected to the lumen 36. As described in greater detail below, the axial passage 40 is formed distal the cutting window 38, and facilitates fluid flow regardless of whether the cutting window 38 is open or closed.

Figure 3A:
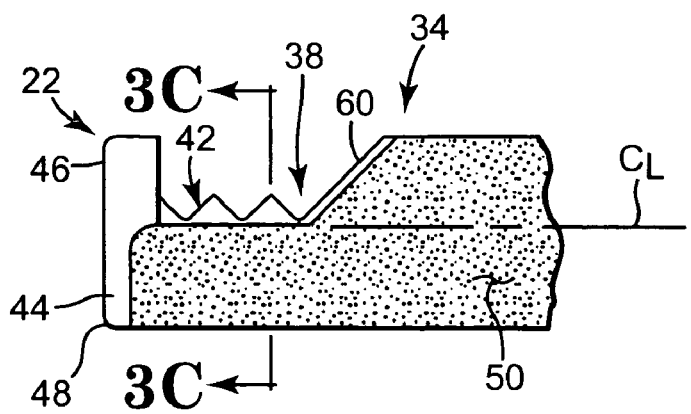
FIG. 3A is an enlarged view of a distal section of the outer tubular member shown in FIG. 2.
Figure 3B:
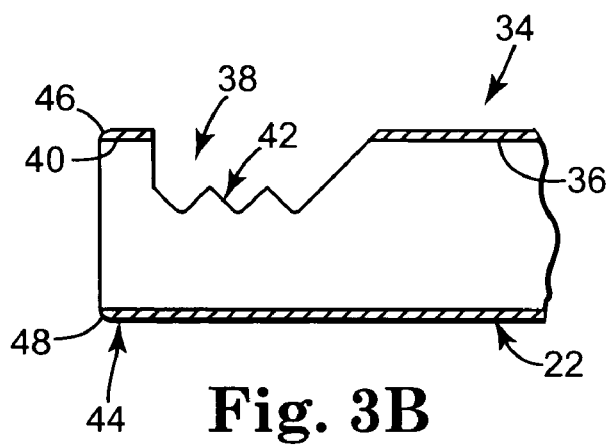
FIG. 3B is a longitudinal cross-sectional view of the distal section of FIG. 3A.
Figure 3C:
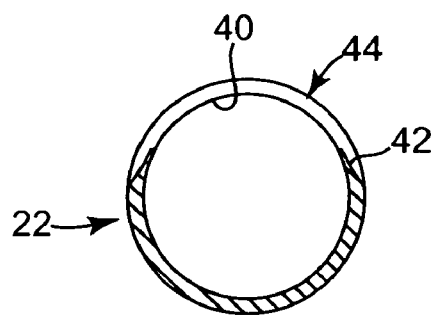
FIG. 3C is a transverse cross-sectional view of the distal section of FIG. 3A.

With additional reference to the views of FIGS. 3A–3C, the distal section 34 forms a cutting surface or edge 42 about at least a portion of the cutting window 38. In one embodiment, the cutting surface 42 is characterized by the formation of teeth. For example, with the embodiment of FIG. 2, two teeth are formed on either side of the cutting window 38. Alternatively, other tooth configurations can be employed. Regardless, the cutting surface 42 defines a perimeter of the cutting window 38, such that the cutting window 38 is open to the lumen 36.

In one embodiment, the axial passage 40 is defined by a ring 44 extending distal the cutting window 38. The axial passage 40 is open to an exterior of the outer tubular member 22, such that material can enter or exit the lumen 36 via the axial passage 40. The ring 44 defines an outer diameter approximating an outer diameter of the distal section 34 immediately proximal the cutting window 38, preferably on the order of approximately 0.1–0.2 inch, more preferably approximately 0.16 inch. Similarly, and as best shown in FIG. 3B, a diameter of the axial passage 40 (i.e., an inner diameter of the ring 44) approximates a diameter of the lumen 36 (i.e., an inner diameter of the distal section 34) immediately proximal the cutting window 38, preferably on the order of 0.1–0.3 inch, more preferably approximately 0.135 inch. As described in greater detail below, the axial passage 40 facilitates fluid flow to the inner tubular member 24. In one embodiment, then, the axial passage 40 has a diameter not less than an inner diameter of the inner tubular member 24 so as to maximize fluid flow. Alternatively, a diameter of the axial passage 40 can assume other forms. Preferably, however, a diameter of the axial passage 40 is not less than one-half a diameter of the lumen 36 immediately proximal the cutting window 38. With this in mind, and with specific reference to FIG. 3C, the ring 44 preferably extends laterally beyond a height of the cutting surface 42. Further, as best shown in FIGS. 3A and 3B, the ring 44 terminates at a radial face 46, defining an axial length of the ring 44 that is less than an axial length of the cutting window 38, preferably on the order of 0.01–0.10 inch, more preferably approximately 0.043 inch. Alternatively, other dimensions are equally acceptable. Regardless, a leading edge 48 of the radial face 46 is preferably beveled or curved so as to minimize potential trauma caused by the leading edge 48 during use.

The outer tubular member 22 is preferably formed of a relatively rigid, electrically conductive material, such as 304L stainless steel. Regardless, an outer surface of the intermediate section 32 and a portion of the distal section 34 is coated or covered with a dielectric insulation material (shown generally at 50 by stippling in FIGS. 2 and 3A). Importantly, the proximal section 30 is preferably free of the dielectric insulation coating 50. The dielectric insulation coating 50 material is preferably a polyolefin coating, but other known dielectric materials can also be employed. In one embodiment, the dielectric coating 50 has a thickness in the range of approximately 0.01–0.03 inch, more preferably 0.02 inch. Further, as best shown by the enlarged view of FIG. 3A, the electrical insulator 50 is not applied to, or does not cover, at least the cutting surface 42 formed by the distal section 34. In one embodiment, additional portions of the distal section 34 are similarly not covered by the electrical insulator 50. In particular, portions of the ring 44 are also exposed. In one embodiment, the insulator material 50 terminates proximal the radial face 46 of the ring 44, such that an entire circumferential section of the ring 44 remains exposed. In one embodiment, the insulator material 50 terminates not less than 0.01 inch from the radial face 46. However, the insulator material 50 preferably extends distal the cutting window 38 a distance of at least 0.01 inch. Additionally, the insulator material 50 follows a shape of a trailing face 60 of the cutting window 38, providing an exposed surface of approximately 0.01 inch in longitudinal width. Relative to the cutting surface 42, the insulator material 50 preferably extends in a linear fashion. For example, in one embodiment where the cutting surface 42 does not project below a centerline $C_L$, the insulator material 50 extends along the centerline $C_L$ as shown in FIG. 3A. Finally, in one embodiment, an entirety of the ring 44 "above" the centerline $C_L$ is not covered by the insulator material 50 (i.e., that portion of the ring 44 extending in a direction of the cutting window 38). With the above dimensions in mind, and in one preferred embodiment, an area of the distal section 34 not covered by the insulator material 50 (i.e., the exposed portion of the distal section 34) has a surface area of less than 0.066 inch$^2$, more preferably approximately 0.063 inch$^2$. This reduced exposed surface area improves the delivery of energy as compared to other devices, as described in greater detail below.

In particular, because portions of the distal section 34 are free of the insulator material 50, an electrical energy, such as radio frequency (RF) energy, otherwise applied to the proximal section 30 propagates to the exposed portion of the distal section 34 for subsequent interaction (e.g., electrocauterization) with contacted tissue (not shown). For example, and referring specifically to FIG. 2, a wire conductor or wiring 70 is preferably fused to the proximal section 30 (that is otherwise free of the insulator material 50). Thus, and in a preferred embodiment, the wiring 70 is permanently electrically connected to the outer tubular member 22. The wire conductor 70 is further connected at an opposite end to an electrical current supply (not shown). Activation of the electrical current supply produces an electrical energy at the exposed portion of the distal section 34. Notably, tissue or other structures otherwise in contact with the outer tubular member 22 at locations other than the exposed portion of the distal section 34 (e.g., covered portions of the distal section 34 and the intermediate section 32) are not affected by the applied current due to the insulator material 50. The insulator material 50 can assume a variety of other electrical insulator forms that otherwise cover a desired region of the outer tubular member 22. For example, the electrical insulator 50 can be a sheath covering the outer tubular member 22.

With continued reference to FIG. 2, the inner tubular member 24 is an elongated tube having a proximal portion 80, a distal portion 82, and a central lumen 84 extending therebetween. The distal portion 82 of the inner tubular member 24 is sized to be received with the lumen 36 of the outer tubular member 22 and, in one embodiment, is formed of a uniform, rigid material, such as 304L stainless steel. Alternatively, the inner tubular member 24 can be configured to effectuate bending thereof, such as by a flexible coupling 86. Examples of available flexible coupling configurations are described, for example, in U.S. Pat. No. 5,922,003, the teachings of which are incorporated herein by reference.

Figure 4:
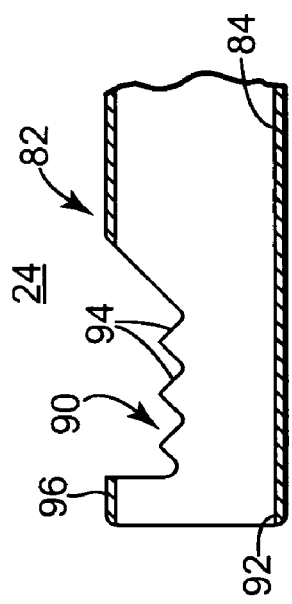
FIG. 4 is an enlarged side view of a distal portion of the inner tubular member of FIG. 2.

Regardless, the distal portion 82 forms a cutting tip 90 and an axial opening 92 as best shown in FIG. 4. The cutting tip 90 and the axial opening 92 are fluidly connected to the central lumen 84, with the cutting tip 90 forming a plurality of teeth 94. In one embodiment, the distal portion 82 of the inner tubular member 24 is highly similar to a configuration of the distal section 34 of the outer tubular member 22, and includes a ring 96 distal the cutting tip 90, with the ring 96 defining the axial opening 92. A diameter of the axial opening 92 (i.e., an inner diameter of the ring 96) preferably approximates a diameter of the central lumen 84 (i.e., an inner diameter of the distal portion 82) immediately proximal the cutting tip 90 to maximize fluid flow through the axial opening 92. Alternatively, other dimensions can be employed. Preferably, however, a diameter of the axial opening 92 is not less than one-half a diameter of the central lumen 84 immediately proximal the cutting tip 90.

In one embodiment, an axial length of the ring 96 of the inner tubular member 24 is slightly less than an axial length of the ring 44 (FIG. 3B) of the outer tubular member 22, for example, on the order of 0.01 inch less in axial length. Alternatively, other dimensions or configurations are acceptable. For example, a structure other than the ring 96 can be employed to define the axial opening 92. In fact, the distal portion 82 can terminate at a distal end of the cutting tip 90, with the axial opening 92 being formed at this distal end. Conversely, the distal portion 90 can be configured to facilitate fluid flow to the central lumen 84 by means other than an axial opening, such that in an alternative embodiment, the axial opening 92 is eliminated.

With specific reference to FIG. 2, the hub assembly 26 includes an outer hub 110, an inner hub 112, and a washer assembly 114 (referenced generally in FIG. 2). As described in greater detail below, the inner hub 112 is adapted to receive the inner tubular member 24. The outer hub 110 is adapted to receive the outer tubular member 22 and the inner hub 112. Finally, the washer assembly 114 is adapted to maintain the inner tubular member 24 relative to the outer tubular member 22 and the outer hub 110.

The outer hub 110 is preferably a molded component forming a shroud portion 120, a wire port 122, and an aspiration port 126. With additional reference to FIG. 5 otherwise illustrating a cross-sectional view of the outer hub 110 assembled to the outer tubular member 22, the outer hub 110 further defines a lumen 128. The lumen 128 includes a proximal section 130 and a distal section 132. As described in greater detail below, the proximal section 130 is sized to receive the inner hub 112, whereas the distal section 132 is sized to receive the proximal section 30 of the outer tubular member 22 and the proximal portion 80 of the inner tubular member 24. The wire port 122 and the aspiration port 126 are each fluidly connected to the lumen 128. Regardless, the outer hub 110 is made of a non-conductive material such that the shroud portion 120 prevents metallic components proximal the shroud portion 120 from contacting metallic implements distal the shroud portion 120 during a surgical procedure.

Upon final assembly of the outer tubular member 22 to the outer hub 110, the proximal section 30 is encompassed within the outer hub 110. Further, the wiring 70 extends through the wire port 122 and is electrically connected to the outer tubular member 22 at the proximal section 30 thereof, not otherwise encompassed by the insulator material 50. In this regard, the outer hub 110 is molded over a connection point 134 between the wiring 70 and the outer tubular member 22. For example, in one embodiment, the outer hub 110 is insert molded over the outer tubular member 22, the wiring 70 and the connection point 134. With this technique, the wiring 70 is permanently electrically connected to the outer tubular member 22. Further, the wire port 122 of the outer hub 110 directs the wiring 70 proximally away from the outer hub 110 and thus the outer tubular member 122. Alternatively, the outer hub 110 can assume a variety of other forms.

Figure 6A:
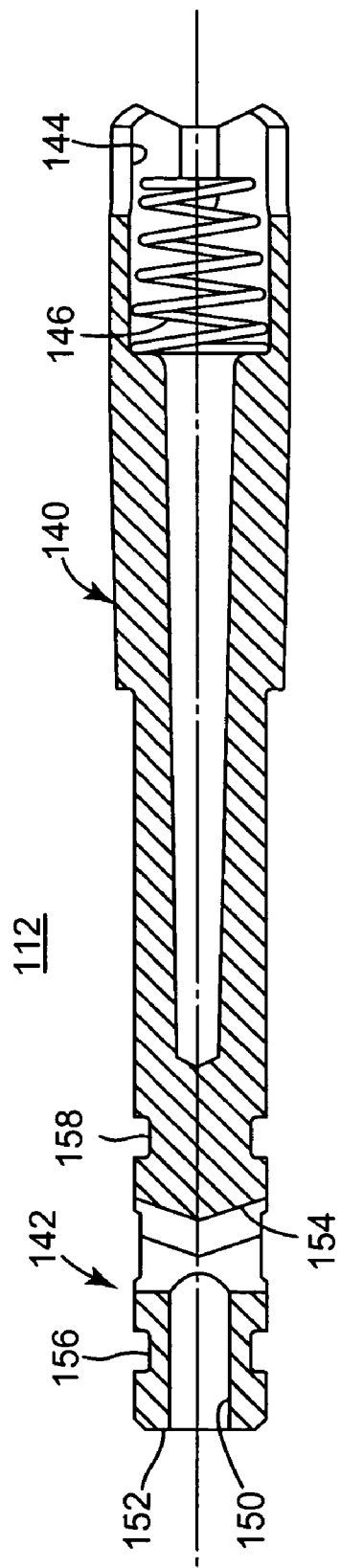
FIG. 6A is a cross-sectional view of an inner hub portion of the instrument of FIG. 1.

Returning to FIG. 2 and with additional reference to FIG. 6A, the inner hub 112 is adapted to receive the inner tubular member 24 and defines a proximal region 140 and a distal region 142. The proximal region 140 is preferably adapted for coupling to a powered surgical handpiece (not shown) and thus, and in one embodiment, forms a connection aperture 144 within which a spring 146 is maintained. Alternatively, the proximal region 140 can assume a variety of other forms. The distal region 142 forms an axial passage 150 extending from a distal end 152 thereof. The axial passage 150 is sized to receive and maintain the proximal portion 80 of the inner tubular member 24. The distal region 142 further includes a radial passage 154 that is fluidly connected to the axial passage 150, as well as first and second circumferential grooves 156, 158 formed distal and proximal the radial passage 154, respectively. As described in greater detail below, the circumferential grooves 156, 158 are sized to receive and maintain sealing components, such as O-rings, for fluidly sealing the radial passage 154 proximal the second circumferential groove 158 and, where desired, distal the first circumferential groove 156.

Figure 5:
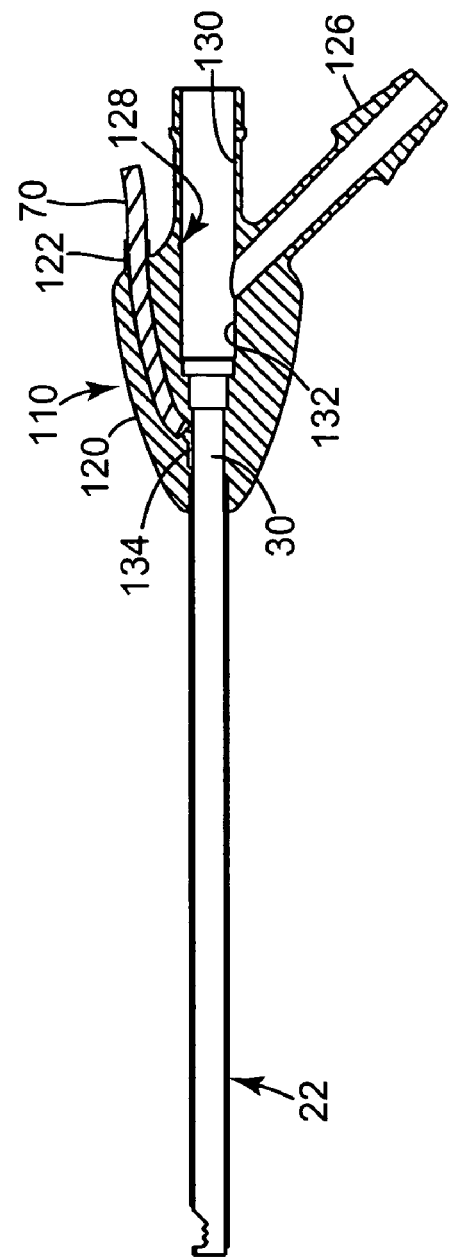
FIG. 5 is a cross-sectional view of outer hub and outer tubular member portions of the instrument of FIG. 1.
Figure 6B:
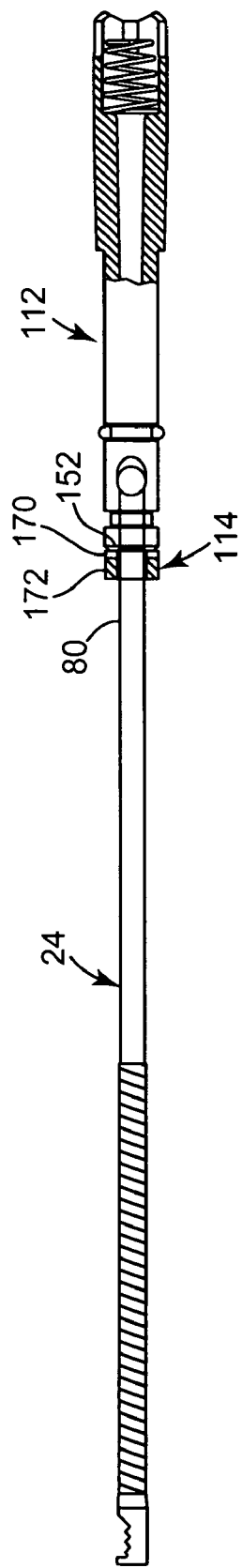
FIG. 6B is a cross-sectional view of the inner hub of FIG. 6A assembled to an inner tubular member.

The washer assembly 114 is best shown in FIG. 6B that otherwise illustrates the inner tubular member 24 assembled to the inner hub 112. In particular, the washer assembly 114 includes, in one embodiment, a first washer 170 and a second washer 172. The first washer 170 is secured over the proximal portion 80 of the inner tubular member 24, and contacts the distal end 152 of the inner hub 112. In this regard, the first washer 170 is preferably adhered to an exterior surface of the inner tubular member 24. The second washer 172 is co-axially received over the proximal portion 80 of the inner tubular member 24, positioned distal the first washer 170 as shown. The first washer 170 is preferably formed of a stainless steel material, whereas the second washer 172 is a high heat-resistant, high strength, high modulus material, preferably an amorphous thermoplastic polyetherimide material, such as Ultem®, available from General Electric Co., of Pittsville, Mass. As described in greater detail below, the one preferred washer assembly 114 provides a bearing surface for the inner tubular member relative to the outer hub 110 (FIG. 5).

Figure 7:
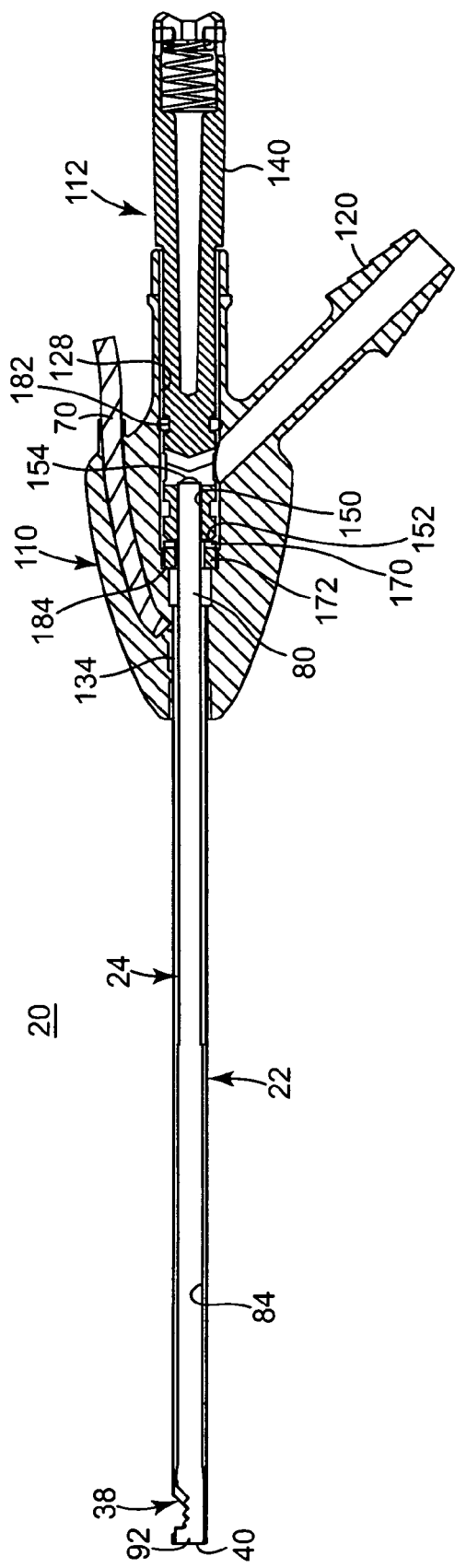
FIG. 7 is a cross-sectional view of the instrument of FIG. 1.

Upon final assembly of the instrument 20, and as shown in FIG. 7, the inner tubular member 24 is coaxially received within the outer tubular member 22. The axial passage 40 (referenced generally in FIG. 7) of the outer tubular member 22 is axially aligned with the axial opening 92 of the inner tubular member 24. The outer tubular member 22 is secured to the outer hub 110, with the insulator material 50 (FIG. 1) covering an exterior surface of the outer tubular member 22 distal the outer hub 110 except for a region adjacent and distal the cutting window 38 as previously described. The wiring 70 is connected to the outer tubular member 22 at the connection point 134 that is otherwise encompassed by the outer hub 110. The inner hub 112 is mounted within the lumen 128 of the outer hub 110, with the proximal region 140 of the inner hub 112 extending proximal the outer hub 110. The inner tubular member 24 is received within the axial passage 150 of the inner hub 112, such that the central lumen 84 of the inner tubular member 24 is fluidly connected to the radial passage 154 of the inner hub 112. The inner hub 112, in turn, in positioned relative to the outer hub 110 such that the aspiration port 126 is fluidly connected to the central lumen 84 of the inner tubular member 24 via the radial passage 154 and the axial passage 150 of the inner hub 112. An O-ring 182 is placed within the second circumferential groove 158 (FIG. 6A), thereby sealing the radial passage 154 relative to the outer hub 110. The first washer 170 is coaxially received over the proximal portion 80 of the inner tubular member 24, and abuts the distal end 152 of the inner hub 112. The second washer 172 distally abuts the first washer 170, and bears against a shoulder 184 formed by the lumen 128 of the outer hub 110. With additional reference to FIG. 8, in one embodiment, the distal portion 82 of the inner tubular member 24 does not bear against the distal section 34 of the outer tubular member 22. Thus, the washer assembly 114 serves as the requisite bearing surface, and controls an axial position of the inner tubular member 24 relative to the outer hub 110 and thus the outer tubular member 22.

Figure 8:
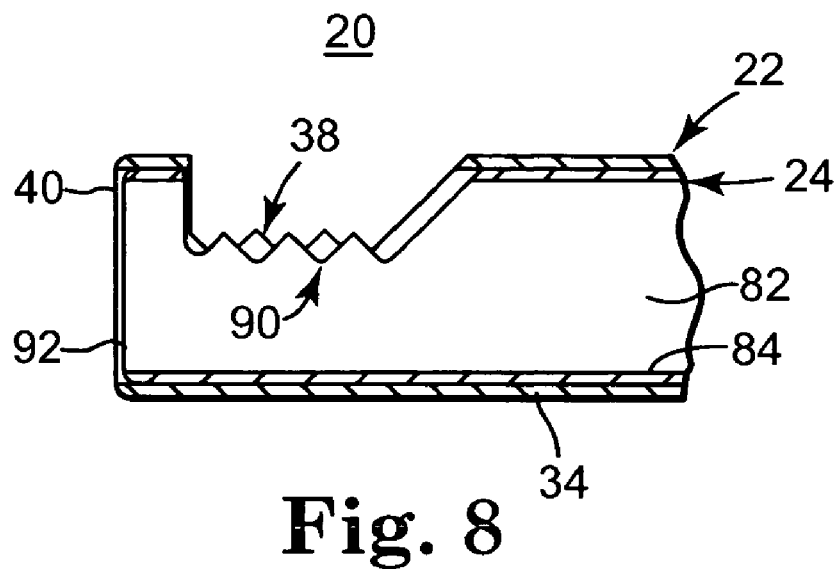
FIG. 8 is an enlarged, cross-sectional view of a distal region of the instrument of FIG. 7 in an open position.

The above-described construction provides for oscillation and/or rotation of the inner tubular member 24 relative to the outer tubular member 22, such as when the inner tubular member is driven by a powered handpiece (not shown) of a type known in the art that is otherwise coupled to the proximal region 140 of the inner hub 112. Further, an essentially continuous flow path is provided from the distal section 34 of the outer tubular member 22, via the central lumen 84 of the inner tubular member 24, to the hub assembly 26 and in particular the aspiration port 126 regardless of rotational or oscillation position of the inner tubular member 24 relative to the outer tubular member 22. For example, in one embodiment, the inner tubular member 24 can be rotated relative to the outer tubular member 22. This rotation renders the cutting window 38 either open or closed. With this in mind, FIG. 8 depicts the cutting window 38 in an "open" position whereby the cutting tip 90 of the inner tubular member 24 is aligned with, or open to, the cutting window 38 of the outer tubular member 22. With this orientation, blood or other bodily tissue can enter the central lumen 84 (caused, for example, by applying a vacuum to the aspiration port 126 (FIG. 7)) via the cutting window 38/cutting tip 90 and the axial passage 40/axial opening 92. Notably, unlike previous designs in which aspiration occurs only through the cutting window 38/cutting tip 90, the preferred relatively large transverse cross-sectional area of the axial passage 40/axial opening 92 facilitates an appreciable increase in aspiration volume.

Figure 9:
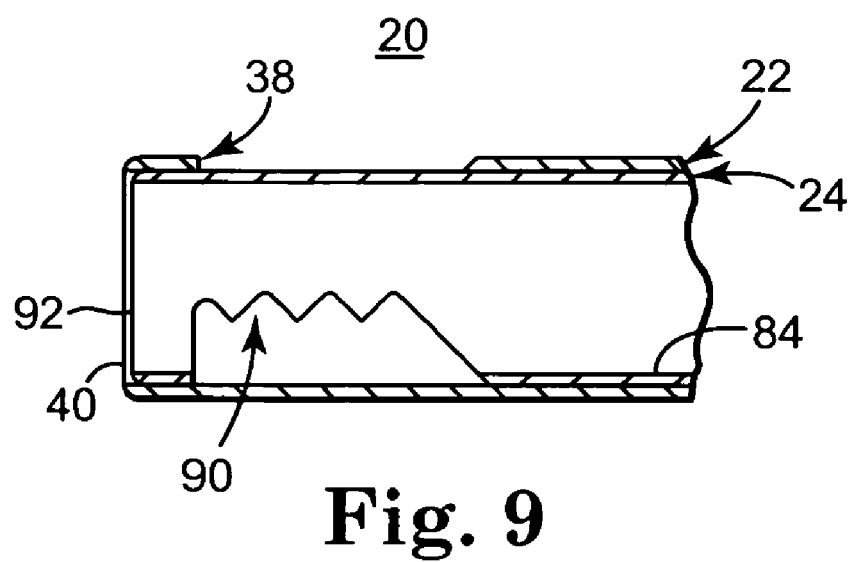
FIG. 9 is an enlarged, cross-sectional view of a distal region of the instrument of FIG. 7 in a closed position.

Conversely, FIG. 9 depicts the inner tubular member 24 rotated approximately 180° from the position of FIG. 8 such that the cutting window 38 is "closed". That is to say, the cutting tip 90 of the inner tubular member 24 is not fluidly aligned with the cutting window 38 such that material cannot enter the central lumen 84 of the inner tubular member 24 via the cutting window 38. However, even in this closed position, the axial passage 40 and the axial opening 92 remain aligned and open to the central lumen 84. Thus, material external the instrument 20 can be aspirated into the central lumen 84 via the axial passage 40/axial opening 92. Effectively, then, in the closed position, the surgical instrument 20 functions like a suction electrocautery device (where energy is applied to the outer tubular member 22) or as a standard suction device when the outer tubular member 22 is not energized.

During use, the surgical micro-resecting instrument 20 is deployed to a target site as commonly done with other cutting instruments. The distal section 34 is positioned within the patient (not shown) such that the cutting window 38 is at the target site. The cutting tip 90 of the inner tubular member 24 is positioned at the cutting window 38 and then driven (e.g., oscillated and/or rotated) relative to the cutting window 38 to resect tissue at the target site, similar to conventional micro-resecting instruments. When it becomes necessary to provide hemostasis at the target site (either during or separate from cutting), an electrical current is applied to the outer tubular member 22 via the wiring 70. In a preferred embodiment, a radio frequency (RF) energy is employed on a monopolar basis. As a general statement, a monopolar electrosurgical instrument includes an active electrode (i.e., the cutting surface 42 and exposed portions of the ring 44 of the outer tubular member 22) for cutting tissue and a remotely located return electrode for providing a return current path. For example, a remote ground pad (not shown), serving as the return electrode, can be attached to the patient's body, such as the thigh or back. The exposed portions of the distal section 34 of the outer tubular member 22 serve as an electrode, cauterizing the contacted tissue to provide hemostasis. Before, during, and/or after resecting or cauterization, blood or other tissue at the target site can be aspirated through the central lumen 84 of the inner tubular member 24 via a vacuum source (not shown) connected to the aspiration port 126. As previously described, when the cutting window is open (i.e., FIG. 8), aspiration occurs through both the cutting window 38 and the axial passage 40. Alternatively, when the cutting window 38 is closed (i.e., FIG. 9), aspiration occurs through the axial passage 40 alone.

Figure 10:
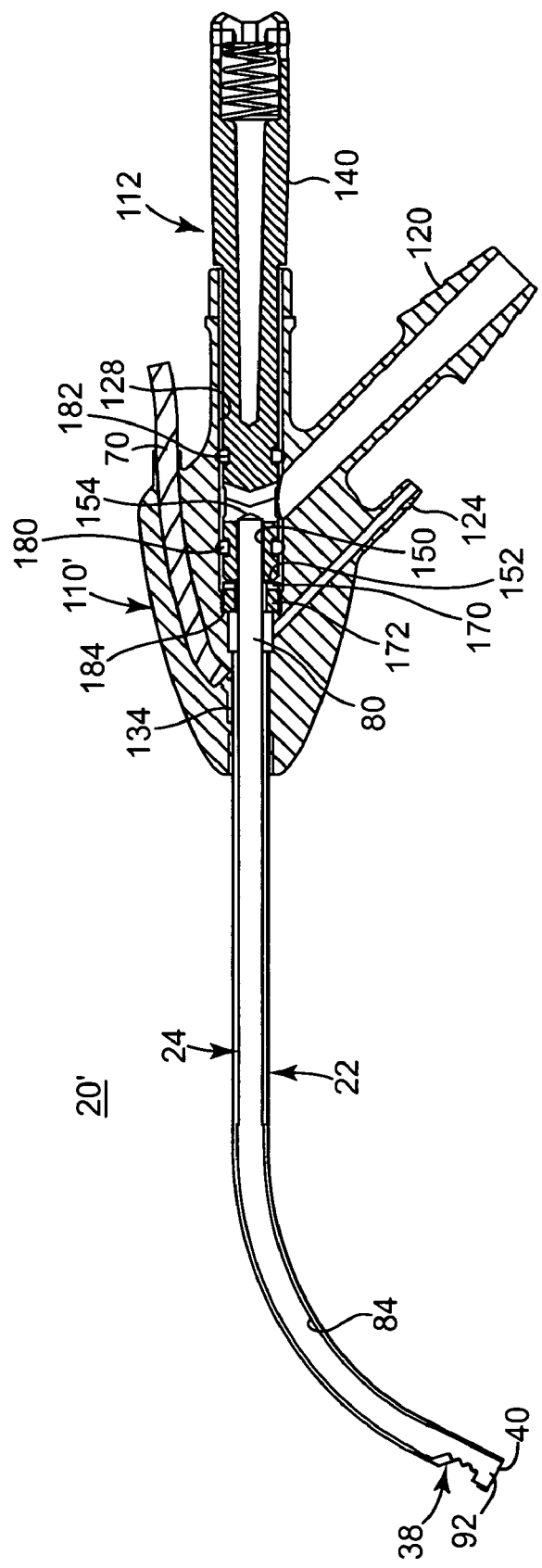
FIG. 10 is a cross-sectional view of an alternative embodiment surgical micro-resecting instrument in accordance with the present invention.

The surgical micro-resecting instrument of the present invention provides a marked improvement over previous designs by providing a single instrument capable of micro-resecting and providing hemostasis, for example, by electrocautery. Further, the surgical instrument of the present invention provides enhanced aspiration regardless of whether the cutting window is open or closed. Notably, the features of the present invention can be achieved with a number of alternative designs. For example, FIG. 10 illustrates an alternative embodiment surgical micro-resecting instrument 20' that is highly similar to previous embodiments, but further includes an irrigation port 124 as part of an outer hub 110'. The irrigation portion 124 is fluidly connected to the lumen 36 of the outer tube 22 within the outer hub 110'. Further, a second O-ring 180 is received within the first circumferential groove 156 of the inner hub 112 to provide an additional seal. Finally, FIG. 10 illustrates the outer tube 22 and the inner tube 24 assuming a curved shape in accordance with the present invention.

Although the present invention has been described with reference to preferred embodiments, workers skilled in the art will recognize that changes can be made in form and detail without departing from the spirit and scope of the present invention.

What is claimed is:

1. A surgical micro-resecting instrument for use with an ENT procedure, the instrument comprising:
    an outer tubular member formed of an electrically conductive material and defining a proximal section, a distal section, and a lumen, wherein the distal section forms a cutting window open to the lumen and a partially enclosed axial passage distal the cutting window, the axial passage being fluidly connected to the lumen;
    an inner tubular member disposed within the lumen of the outer tubular member, the inner tubular member defining a proximal portion and a distal portion, wherein the distal portion forms a cutting tip;
    a hub assembly maintaining the proximal section of the outer tubular member and the proximal portion of the inner tubular member; and
    an electrical insulator covering a region of the outer tubular member distal the hub assembly, wherein at least the cutting window is not covered by the insulator.

2. The instrument of claim 1, wherein the distal section of the outer tubular member includes a ring distal the cutting window, the ring defining the axial passage.

3. The instrument of claim 2, wherein at least a portion of the ring is not covered by the insulator.

4. The instrument of claim 3, wherein the ring terminates in a radial face, and further wherein at least the radial face is not covered by the insulator.

5. The instrument of claim 4, wherein the insulator covers a portion of the ring proximal the radial face and distal the cutting window.

6. The instrument of claim 5, wherein the insulator extends at least 0.01 inch distal the cutting window.

7. The instrument of claim 5, wherein an axial length of at least 0.01 inch of the ring proximal the radial face is not covered by the insulator.

8. The instrument of claim 2, wherein the ring has a diameter equal to a diameter of the outer tubular member immediately proximal the cutting window.

9. The instrument of claim 1, wherein an exposed exterior surface area of the distal section of the outer tubular member is less than 0.066 inch$^2$.

10. The instrument of claim 1, wherein the axial passage has a diameter not less than one-half a diameter of the lumen.

11. The instrument of claim 10, wherein the diameter of the axial passage approximates the diameter of the lumen immediately proximal the cutting window.

12. The instrument of claim 1, wherein the outer tubular member forms teeth along a perimeter of the cutting window.

13. The instrument of claim 1, wherein the inner tubular member forms a central lumen and an axial opening distal the cutting tip, the axial opening being fluidly connected to the central lumen.

14. The instrument of claim 13, wherein the distal portion of the inner tubular member includes a ring distal the cutting tip, the ring defining the axial opening.

15. The instrument of claim 13, wherein the instrument is configured such that upon final assembly, the axial passage of the outer tubular member remains open to the central lumen of the inner tubular member regardless of a rotational position of the distal portion of the inner tubular member.

16. The instrument of claim 1, wherein the hub assembly includes:
an outer hub connected to the proximal section of the outer tubular member;
an inner hub connected to the proximal portion of the inner tubular member; and
a washer assembly disposed over the proximal portion of the inner tubular member, the washer assembly providing a bearing surface for movement of the inner tubular member relative to the outer tubular member.

17. The instrument of claim 16, wherein upon final assembly, the washer assembly contacts the outer hub.

18. The instrument of claim 17, wherein the washer assembly includes a first washer abutting a distal end of the inner hub and a second washer distal the first washer.

19. The instrument of claim 18, wherein the second washer is comprised of an amorphous thermoplastic polyetherimide material.

20. A surgical micro-resecting system comprising:
a micro-resecting instrument including:
an outer tubular member formed of an electrically conductive material and defining a proximal section, a distal section, and a lumen, wherein the distal section forms a cutting window open to the lumen and an axial passage distal the cutting window, the axial passage being fluidly connected to the lumen;
an inner tubular member disposed within the lumen of the outer tubular member, the inner tubular member defining a proximal portion and a distal portion, wherein the distal portion forms a cutting tip;
a hub assembly maintaining the proximal section of the outer tubular member and the proximal portion of the inner tubular member; and
an electrical insulator covering a region of the outer tubular member distal the hub assembly, wherein at least the cutting window is not covered by the insulator;
a powered surgical handpiece coupled to the proximal portion of the inner tubular member for driving the inner tubular member relative to the outer tubular member;
an energy source; and
wiring electrically connecting the energy source to the outer tubular member.

21. The system of claim 20, further comprising:
a vacuum source connected to the hub assembly;
wherein the hub assembly fluidly connects the vacuum source to a central lumen of the inner tubular member.

22. The system of claim 20, wherein the distal section of the outer tubular member includes a ring distal the cutting window, the ring defining the axial passage.

23. The system of claim 22, wherein the ring terminates in a radial face, and further wherein at least the radial face is not covered by the insulator.

24. The system of claim 20, wherein the axial passage has a diameter not less than one-half a diameter of the lumen.

25. The system of claim 20, wherein the outer tubular member forms teeth along a perimeter of the cutting window.

26. The system of claim 20, wherein the inner tubular member forms a central lumen and an axial opening distal the cutting tip, the axial opening being fluidly connected to the central lumen.

27. The system of claim 26, wherein the instrument is configured such that the axial passage of the outer tubular member remains open to the central lumen of the inner tubular member regardless of a rotational position of the cutting tip relative to the cutting window.

28. The system of claim 27, wherein the hub assembly includes:
an outer hub connected to the proximal section of the outer tubular member;
an inner hub connected to the proximal portion of the inner tubular member;
a first washer co-axially received over the inner tubular member and abutting a distal end of the inner hub; and
a second washer co-axially received over the inner tubular member distal the first washer.

29. A method for performing a micro-resecting operation at a target site of a patient as part of an ENT surgical procedure, the method comprising:
providing a micro-resecting instrument including an outer tubular member having a lumen and a distal section forming a cutting window and a partially enclosed axial passage distal the cutting window, the cutting window and the axial passage being fluidly connected to the lumen, an inner tubular member disposed within the lumen and having a distal portion forming a cutting tip, a hub assembly maintaining the proximal section of the outer tubular member and the proximal portion of the inner tubular member, and an electrical insulator covering a region of the outer tubular member distal the hub assembly such that at least the cutting window is not covered by the insulator;
delivering the distal section of the outer tubular member to the target site such that the cutting window is located at the target site and the cutting tip is located within the cutting window;
driving the inner tubular member relative to the outer tubular member such that the cutting tip resects tissue at the target site to effectuate a portion of an ENT procedure;
supplying energy to an exposed region of the distal section of the outer tubular member; and
cauterizing tissue at the target site via the energized exposed region.

30. The method of claim 29, further comprising:
selectively coupling the micro-resecting instrument to a powered surgical handpiece.

31. The method of claim 29, further comprising:
aspirating material from the target site into the instrument via the axial passage.

32. The method of claim 31, wherein the inner tubular member defines a central lumen, and further wherein material is aspirated through the axial passage into the central lumen.

33. The method of claim 32, wherein the inner tubular member forms an axial opening distal the cutting tip, the axial opening being fluidly connected to the central lumen of the inner tubular member, and further wherein material is aspirated through the axial opening into the central lumen.

34. The method of claim 32, wherein material is further aspirated into the central lumen via the cutting window.

35. The method of claim 32, further comprising:
orienting the inner tubular member relative to the outer tubular member such that the cutting window is closed;

wherein aspirating material into the central lumen occurs while the cutting window is closed.

36. The method of claim 31, wherein aspirating material into the instrument occurs apart from supplying energy to an exposed region of the distal section.

37. The method of claim 29, wherein the axial passage has a transverse diameter not less than one-half a diameter of the lumen immediately proximal the cutting window.

* * * * *